United States Patent
Kerrigan et al.

(10) Patent No.: US 9,040,514 B2
(45) Date of Patent: May 26, 2015

(54) CHLOROBIS COPPER (I) COMPLEX COMPOSITIONS AND METHODS OF MANUFACTURE AND USE

(75) Inventors: Sean Kerrigan, Champaign, IL (US); Nolan Mente, Pella, IA (US); Charles Louis Albartus Barker, Flagstaff, AZ (US)

(73) Assignee: C LAB PHARMA INTERNATIONAL, S.A., Tortola (VG)

( * ) Notice: Subject to any disclaimer, the term of this patent is extended or adjusted under 35 U.S.C. 154(b) by 0 days.

(21) Appl. No.: 14/237,876

(22) PCT Filed: Aug. 9, 2012

(86) PCT No.: PCT/US2012/050212
§ 371 (c)(1),
(2), (4) Date: May 16, 2014

(87) PCT Pub. No.: WO2013/023104
PCT Pub. Date: Feb. 14, 2013

(65) Prior Publication Data
US 2014/0243301 A1 Aug. 28, 2014

Related U.S. Application Data (60) Provisional application No. 61/521,698, filed on Aug. 9, 2011.

(51) Int. Cl.
| | | |
|---|---|---|
| *A61K 31/555* | (2006.01) | |
| *C07F 1/08* | (2006.01) | |
| *A61K 31/30* | (2006.01) | |
| *A61K 31/444* | (2006.01) | |
| *C07F 1/00* | (2006.01) | |

(52) U.S. Cl.
CPC . *C07F 1/08* (2013.01); *A61K 31/30* (2013.01); *A61K 31/444* (2013.01); *C07F 1/005* (2013.01)

(58) Field of Classification Search
USPC .............................. 514/188; 546/2
See application file for complete search history.

(56) References Cited

U.S. PATENT DOCUMENTS

| | | |
|---|---|---|
| 2009/0105207 A1 | 4/2009 | Hussein et al. |
| 2011/0136776 A1 | 6/2011 | Hussein Aly Ibraheim |
| 2011/0183951 A1 | 7/2011 | Hussein |
| 2011/0274773 A1 | 11/2011 | Hussein Aly Ibraheim |
| 2013/0184247 A1 | 7/2013 | Hussein Aly Ibraheim |

FOREIGN PATENT DOCUMENTS

WO 2010/009739 A1 1/2010

OTHER PUBLICATIONS

El-Saadani, M.A. et al.: The protective effect of copper complexes against gastric mucosal ulcer in rats. Biochem. Pharmacol. vol. 46, pp. 1011-1018, 1993.*
Goher, M.A. : Crystal structure of a polymeric 2:1 complex of nicotinic acid with copper(I)chloride. Inorganica Chimica Acta. , vol. 127, pp. L13-L16, 1987.*
International Search Report and Written Opinion of the International Searching Authority for PCT/US2012/050212 dated Dec. 20, 2012.
El-Saadani, "A combination therapy with copper nicotinate complex reduces the adverse effects of 5-fluorouracil on patients with hepatocellular carcinoma", Journal of Experimental Therapeutics and Oncology, 4(1):19-24 (2004).
Salama et al., "A novel therapeutic drug (copper nicotinic acid complex) for non-alcoholic fatty liver", Liver International, 27(4):454-464 (May 2007).
European Search Report for corresponding EP Application No. 12822276.7 dated Feb. 4, 2015.

* cited by examiner

*Primary Examiner* — Charanjit Aulakh
(74) *Attorney, Agent, or Firm* — Rodney J. Fuller; Booth Udall Fuller, PLC (57) ABSTRACT

A method of manufacturing an anhydrous copper complex of formula $C_{12}H_{10}ClCuN_2O_4$ and methods of treating neuromuscular and other diseases, including but not limited to fibromyalgia, multiple sclerosis, muscular dystrophy, rheumatoid arthritis, pain, fatigue, sleeplessness, loss of fine motor control, speech loss, inflexibility, Alzheimer's, dementia, amyotrophic lateral sclerosis, depression, lyme disease, lyme disease co-infection, gastroparesis (GP), myopathy, chronic inflammation and/or incontinence. The anhydrous copper complex preferably is administered in a pharmaceutical and/or dietary supplement composition of the invention.

5 Claims, 9 Drawing Sheets

Quantitative Results for: 128g1m1(2)

| Element Line | Net Counts | Weight % | Weight % Error | Atom % | Atom % Error | Formula | Compnd % |
|---|---|---|---|---|---|---|---|
| N K | 0 | 0.00 | --- | 0.00 | +/- 0.00 | N2O5 | 0.00 |
| O K | 2892 | 5.89S | --- | 15.11 | +/- 0.24 | | --- |
| Cl K | 1342 | 47.28 | +/- 1.55 | 54.68 | +/- 1.79 | Cl | 47.28 |
| Cu K | 302 | 46.82 | +/- 9.15 | 30.21 | +/- 5.90 | Cu2O | 52.72 |
| Total | | 100.00 | | 100.00 | | | 100.00 |

CHLOROBIS COPPER (I) COMPLEX COMPOSITIONS AND METHODS OF MANUFACTURE AND USE

RELATED APPLICATION DATA

This application is the U.S. National Stage of International Application No. PCT/US2012/050212, filed Aug. 9, 2012, which claims the benefit of U.S. Provisional Application No. 61/521,698 filed Aug. 9, 2011, each of which is hereby incorporated by reference in their entireties.

BACKGROUND OF THE INVENTION

1. Field of the Invention

The present invention is directed to pharmaceutical and/or dietary supplement compositions and methods of treating neuromuscular and other diseases, including but not limited to fibromyalgia, multiple sclerosis, muscular dystrophy, Alzheimer's, dementia, amyotrophic lateral sclerosis, depression, and/or rheumatoid arthritis. The present invention also encompasses pharmaceutical and/or dietary supplement compositions and methods of treating other physical ailments and disorders, including but not limited to pain, fatigue, sleeplessness, loss of fine motor control, speech loss, inflexibility, lyme disease, lyme disease co-infection, gastroparesis (GP), myopathy, chronic inflammation and/or incontinence. The method typically comprises administration to a subject in need thereof an anhydrous copper complex of formula $C_{12}H_{10}ClCuN_2O_4$. The invention also generally relates to pharmaceutical treatment regimes and methods of making the anhydrous copper complex of the present invention.

2. Discussion of the Background

A litany of human diseases and other ailments are characterized by neuromuscular degeneration and muscle weakness. The term "neuromuscular disease" refers to disorders that adversely affect muscle function and/or the control thereof by the central nervous system (CNS). In general, neuromuscular diseases encompass a wide range of physical ailments characterized by impaired muscle function. The following (non-limiting) list of conditions is generally recognized as neuromuscular diseases or conditions: multiple sclerosis, muscular dystrophy, rheumatoid arthritis, fibromyalgia, myopathy, inflammatory bowel disease (IBD), incontinence, inflexibility, impaired fine motor skills, and amyotrophic lateral sclerosis ("ALS" or Lou Gehrig's disease).

A stroke, formerly known as a cerebrovascular accident (CVA), often results in severe neurological impairment. Post-stroke, many individuals suffer one or more neurological impairments including, but not limited to: loss of fine motor control, paralysis, speech impairment/loss (aphasia and/or dysarthria), altered smell, taste, hearing, or vision, ptosis, ocular and facial muscle weakness, diminished reflexes, loss of balance, altered heart rate, apraxia, loss of memory, and/or confusion.

Numerous therapeutic methodologies are presently available for the treatment of neurological conditions such as the ones listed above. Efficacious treatments have proven elusive, however, and existing drugs with the most promise often exhibit the most undesirable side effects.

Two of the most prominent diseases associated with impaired neurological function are MD, MS and RA. These diseases and currently available treatments therefore, are discussed in greater detail herein below.

Muscular Dystrophy

The term Muscular Dystrophy (MD) actually refers to a group of diseases characterized by muscle weakness and/or impaired muscle function. The specific diseases include, but are not limited to Becker, Duchenne, and Emery-Dreifuss. Over 100 diseases, however, display symptoms similar to MD. All are characterized by reduced muscle function and muscle weakness.

No cure exists for MD and many of the related pathologies. Physical and occupational therapy may help those afflicted with MD manage life with the disease, but neither therapy ameliorates or reverses the disease's underlying causes or symptoms. Antisense oligonucleotides have shown promise as a treatment, but are costly and difficult to obtain for many MD patients. As a result, a significant need exists for a cost-effective, widely available treatment for MD (and related pathologies).

Multiple Sclerosis

Multiple Sclerosis (MS) is an autoimmune disease diagnosed in 350,000-500,000 people in the United States. The disease is characterized by multiple areas of inflammation and scarring of the myelin in the brain and spinal cord. Patients inflicted with the disease exhibit varying degrees of neurological impairment depending on the location and extent of the myelin scarring. Typical MS symptoms include fatigue, weakness, spasticity, balance problems, bladder and bowel problems, numbness, loss of vision, tremors, and depression. Available treatments of MS generally only alleviate symptoms or delay the progression of the disability. Recently developed treatments for MS (including stem cell implantation and gene therapy) appear to be only conservatory. Consequently, improved approaches for the treatment of MS are needed.

Rheumatoid Arthritis

Rheumatoid Arthritis (RA) is another troublesome disorder associated with inflammation. It is signified by chronic inflammation in the membrane lining (the synovium) of the joints and/or other internal organs. These inflammatory cells can also damage bone and cartilage. For example, a joint inflicted with RA may lose its shape and alignment, which can result in the loss of range of motion. RA is characterized by pain, stiffness, warmth, redness and swelling in the joint, and other systemic symptoms like fever, fatigue, and anemia. RA currently affects roughly 1% of the entire U.S. population (approximately 2.2 million people). The pathology of RA is not fully understood, although it has been hypothesized to result from a cascade of aberrant immunological reactions.

In many cases, conventional treatments for RA have proven inefficient. For example, RA responds only partially to symptomatic medications such as corticosteroids and non-steroidal anti-inflammatory drugs (NSAIDs). These medications have been around since the 1950's, and possess a significant risk of contraindications. Moreover, the therapeutic effects of anti-rheumatic drugs (DMARDs) such as Methotrexate (MTX) are frequently inconsistent and only temporary. The latest class of "biologic" DMARDs (including ENBREL®, REMICADE®, HUMIRA®, and KINERET®) have shown promising treatment results, but significant concerns exist regarding their long term safety profile. For example, studies have shown an association between the use of both ENBREL® or REMICADE® and the development of lymphoma. Other reports have demonstrated that patients treated with either drug exacerbate their congestive heart failure and develop serious infection and sepsis, and aggravate symptoms of MS and other central nervous system problems. As with MS, a need exists for more effective treatments of RA.

Lyme Disease

Lyme disease is a bacterial infection (*borrelia burgdorferi*) spread by ticks. The number of reported cases of Lyme disease, and the number of geographical areas in which it is found, has been increasing. In addition to causing arthritis, lyme disease can also cause heart, brain, and nerve problems. Early symptoms include skin-rash, flu-like symptoms (.e.g. chills, fever, swollen lymph nodes, headaches, fatigue, muscle aches/pains, and joint pain). More advanced symptoms include nerve problems and arthritis. Currently, there is no available vaccine on the market in the US for lyme disease.

Lyme Disease Co-Infection

Often, ticks can become infected with multiple disease-causing microbes, resulting in co-infection. This may be a potential problem for humans, due to Borrelia burgdorferi, and other harmful pathogens carried and transmitted by some ticks. Possible co-infections with viruses such as lyme borreliosis, anaplasmosis, babesiosis, or encephalitis may occur. It is not known how co-infection may affect disease transmission and progression, but may help in diagnosing and treating lyme and other such diseases. Currently, there is no reliable and regular treatment for lyme disease co-infection.

Gastroparesis

Gastroparesis is a condition characterizes by the inability of the stomach to empty its contents, when there is no blockage (obstruction). The cause of gastroparesis is not known. There is some evidence that it may be caused by a disruption of nerve signals to the stomach. The condition is a complication of diabetes and of some surgeries. Risk factors associated with gastroparesis may include diabetes, gastrectomy (surgery to remove part of the stomach), systemic sclerosis, use of medication that blocks certain nerve signals (anticholinergic medication). Symptoms may include abdominal distention, hypoglycemia (in people with diabetes), nausea, premature abdominal fullness after meals, weight loss, and vomiting. If gastroparesis is caused by a condition that is reversible (e.g. pancreatitis), when the condition is resolved, the symptoms will subside. For some diabetics, better control of their blood sugar can also improve the symptoms. If there is no reversible cause, gastroparesis rarely resolves itself and the symptoms often grow more sever with time. When accompanied by motility disorders of the muscles of the small intestine, gastroparesis is particularly difficult to treat.

SUMMARY OF THE INVENTION

The objective of the present invention is to provide pharmaceutical and/or dietary supplement compositions and methods of making and using the same to treat and reduce many of the symptoms of several diseases. The compositions contain an active pharmacological ingredient comprised of a novel anhydrous copper complex of formula $C_{12}H_{10}ClCuN_2O_4$. The pharmacologically active ingredient may be administered alone or in combination with additional active or inert agents or therapies (e.g. other anti-inflammatory agents, diluents, and/or excipients).

The pharmacologically active ingredient of the present invention possesses the following chemical structure, referred to herein as Formula I:

The present invention is also directed to a method of treating diseases and other physical ailments or disorders. In a preferred embodiment the method comprises the step of administering to a subject in need thereof an anhydrous copper complex of formula $C_{12}H_{10}ClCuN_2O_4$ to reduce and/or treat a disease or physical ailment or disorder. Preferably the disease or physical ailment being treated is a neuromuscular disease. The treated diseases or disorders (or other physical ailments) include, but are not limited to: fibromyalgia, spinal cord injury, multiple sclerosis, muscular dystrophy, stroke, rheumatoid arthritis, pain, fatigue, sleeplessness, loss of fine motor control, speech loss, inflexibility, lyme disease, lyme disease co-infection, gastroparesis (GP), chronic inflammation, myopathy, chronic inflammation, and/or incontinence. It is also preferable that the subject be diagnosed with one of the diseases and/or disorders prior to treatment. Preferred embodiments of the compositions of the present invention, including recommended dosages and methods of use, are more fully described below in the Detailed Description.

BRIEF DESCRIPTION OF THE DRAWINGS

Illustrative and exemplary embodiments of the invention are shown in the drawings in which.

Elements and facts in the figures are illustrated for simplicity and have not necessarily been rendered according to any particular sequence or embodiment.

DETAILED DESCRIPTION OF THE PREFERRED EMBODIMENTS

Chemical Structure and Properties:

The present invention is directed to pharmaceutical and/or dietary supplement compositions for treating a neuromuscular disease or other disorder. The diseases capable of treatment by the compositions of the present invention include, but are not limited to: fibromyalgia, multiple sclerosis, muscular dystrophy, rheumatoid arthritis, Alzheimer's, dementia, amyotrophic lateral sclerosis ("ALS" or Lou Gehrig's disease), amyotrophic lateral sclerosis, depression, pain, fatigue, sleeplessness, loss of fine motor control, speech loss, inflexibility, lyme disease, lyme disease co-infection, gastroparesis (GP), myopathy, chronic inflammation, incontinence and/or depression. The treatment of the present invention comprises administering to a subject in need thereof a compound of formula $C_{12}H_{10}ClCuN_2O_4$, preferably the chemical structure is of Formula I:

The present invention is further directed to pharmaceutical and/or dietary supplement compositions for treating a physical ailment or disorder including, but not limited to: stroke, pain, fatigue, sleeplessness, inflexibility, myopathy, incontinence, impaired fine motor skills, high cholesterol, low sperm count, obesity, alopecia, burns, stretch marks, scars, Attention Deficit Disorder (ADD), Attention Deficit Hyperactivity Disorder (ADHD), and erectile dysfunction. The treatment of the present invention comprises administering to a subject in need thereof a compound of formula $C_{12}H_{10}ClCuN_2O_4$ (e.g., "Formula I"):

Preferably the subject is first diagnosed with one of the disease listed above before treatment.

In an alternate embodiment, the present invention is further directed to pharmaceutical and/or dietary supplement compositions for treating post-stroke symptoms, including, but not limited to: loss of fine motor control, paralysis, speech impairment/loss (aphasia and/or dysarthria), altered smell, taste, hearing, or vision, ptosis, ocular and facial muscle weakness, diminished reflexes, loss of balance, altered heart rate, apraxia, loss of memory, and/or confusion. The treatment of the present invention comprises administering to a subject in need thereof a compound of formula Cl2H10ClCuN2O4 (e.g., "Formula I"):

Formula I

Advantageously, the present invention is further directed to pharmaceutical and/or dietary supplement compositions for promoting one or more desired health benefits. In a preferred embodiment, the compositions of the present invention promote hair growth, skin healing, scar removal, nerve growth, muscle growth, enhanced athletic performance, reduced post-traumatic healing time, post-surgery healing, and/or enhanced libido.

Optionally, the compositions of the present invention are used in combination with additional active or inert agents or alternative therapies (e.g. other anti-inflammatory agents, diluents, and/or excipients). In a preferred embodiment, the alternative therapy is ozone therapy. Preferably, use of the compositions of the present invention enhances the effectiveness of the alternative therapy.

Preparations and Administrations:

The invention may be used to treat an animal with a disease or physical ailment or disorder including, but not limited to, one or more of the following: fibromyalgia, multiple sclerosis, muscular dystrophy, rheumatoid arthritis, Alzheimer's, dementia, ALS, depression, pain, fatigue, sleeplessness, inflexibility, myopathy, lyme disease, lyme disease co-infection, gastroparesis (GP), chronic inflammation, incontinence, impaired fine motor skills, high cholesterol, low sperm count, obesity, alopecia, burns, stretch marks, scars, ADD, ADHD, and/or erectile dysfunction, wherein it is preferable that the animal is a mammal and more preferable that the mammal is a human.

Formula I is comprised of an anhydrous chlorobis copper I complex (nicotinic acid). Preferably, the pharmaceutical composition containing an effective amount of Formula I further comprises copper ascorbate (esterified Vitamin C), ascorbic acid (Vitamin C), and/or a pharmaceutically acceptable excipient (carrier). More preferably, the pharmaceutically acceptable carrier is an inert diluent.

Frequency of dosage may vary depending on the purity of the compound and the particular disease or physical ailment treated. However, for treatment of most diseases and physical ailments, a dosage regimen of (4) 2.5 mg capsules (for a total of 10 mg/day) containing Formula I is preferred. As will be understood by one skilled in the art, however, the optimal dosage level for a particular subject will vary depending on a plurality of factors including the potency and activity of the pharmacologically active ingredient (e.g., Formula I), as well as the age, body weight, general health, sex, diet, time of administration, route of administration and rate of excretion, drug combination (if any) and the severity of the particular disease or physical ailment undergoing therapy. Subject to the above factors, a generally effective amount of Formula I is between 1 mg and 20 mg per day. More preferably, the effective amount of Formula I is between 5 mg and 10 mg per day. Advantageously, the effective amount of Formula I is between 7.5 mg to 10 mg per day. Most preferably (subject to the factors listed above), the effective amount of Formula I is 10 mg/per day.

Formula I may also comprise a component of an overall pharmaceutical treatment regime for reducing and/or treating a disease or physical ailment or other disorder including, but not limited to: fibromyalgia, multiple sclerosis, muscular dystrophy, rheumatoid arthritis, Alzheimer's, dementia, ALS, depression, pain, fatigue, sleeplessness, inflexibility, myopathy, incontinence, impaired fine motor skills, high cholesterol, low sperm count, obesity, alopecia, burns, stretch marks, scars, ADD, ADHD, and/or erectile dysfunction, the treatment regime comprising: administering to a subject at the least the following pharmacologically active ingredient(s) within a 24-hour period: a compound of Formula I, and optionally a pharmaceutically acceptable carrier, wherein the pharmacologically active ingredient(s) is in an amount sufficient to reduce the symptoms of the ailment.

Optionally, the pharmaceutical treatment regime including Formula I may include (or be combined with) additional pharmacologically active ingredients or other complementary treatments in order to provide synergistic therapeutic effects. For example, Formula I may be administered in combination with additional pharmacologically active agents including, but not limited to, non-steroidal anti-inflammatory drugs (NSAIDs), corticosteroids, disease modifying anti-rheumatic drugs (DMARDs), biologic DMARDs, and/or cyclooxygenase-2 (COX-2) inhibitors. In a preferred embodiment, Formula I is administered in combination with ozone therapy.

The pharmaceutical and/or dietary supplement compositions (containing Formula I) of the present invention may take a variety of forms specially adapted to the chosen route of administration. The compositions may be administered orally, topically, parenterally, by inhalation or spray, or by any other conventional means. Preferably, the compositions are prepared and administered in dosage unit formulations containing conventional non-toxic pharmaceutically acceptable carriers, adjuvants and vehicles. In one preferred embodiment, the composition is administered sublingually. It is further understood that the preferred method of administration may be a combination of methods. Oral administration in the form of a capsule, pill, elixir, syrup, lozenge, troche, or the like is particularly preferred. The pharmaceutical compositions of the present invention (containing Formula I) are preferably in a form suitable for oral use, for example, as tablets, troches, lozenges, aqueous or oily suspensions, dispersible powders or granules, emulsion, hard or softgel capsules, or syrups or elixirs.

Compositions intended for oral use may be prepared according to any method known in the art for manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients suitable for the manufacture of tablets. Such excipients may include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by techniques to delay disintegration and absorption in the gastrointestinal tract and thereby provide a sustained action over a longer period. For example, a time delay material such as glyceryl monostearate or glyceryl distearate may be utilized.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of ethylene oxide with long chain aliphatic alcohols—for example, heptadecaethyleneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid and/or copper ascorbate.

Dispersible powders and granules suitable for preparation of an aqueous suspension by the addition of water provide the active ingredient (Formula I) in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth; naturally-occurring phosphatide, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring or coloring agents. The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- and diglycerides. In addition, fatty acids such as oleic acid find use in the preparation of injectables.

Alternatively, the compositions can be administered parenterally in a sterile medium. Formula I, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing Formula I may be added to the animal's feed or drinking water. Optionally, one skilled in the art will recognize that animal feed and drinking products may be formulated such that the animal takes in an effective amount of Formula I via their diet. For example, Formula I may constitute a component of a premix formulated for addition to the feed or drinking water of an animal. Compositions containing Formula I may also be formulated as food or drink supplements for humans.

Preferred embodiments of compositions containing Formula I will have desirable pharmacological properties that include, but are not limited to, oral bioavailability, low toxicity, and desirable in vitro and in vivo half-lives. The half-life of Formula I is inversely proportional to the frequency of dosage of Formula I.

It is to be understood that the foregoing describes preferred embodiments of the present invention and that modifications may be made thereto without departing from the scope or spirit of the present invention as set forth in the claims. Such scope is limited only by the claims below as read in connection with the above specification. Many additional advantages of applicant's invention will be apparent to those skilled in the art from the descriptions, drawings, and the claims set forth herein.

Representative Elemental and SEM Analysis

The following Tables (1-2) illustrate the results of an elemental analysis of a composition comprising Formula I. The elemental analysis depicts only one preferred embodiment of the invention and is no way intended to limit the scope of the invention.

TABLE 1

| | Run 1 | | |
|---|---|---|---|
| Element | Theoretical | Found | Diff |
| Cu | 18.41% | 15.73% | −2.68 |

TABLE 2

| | | Run 29129 | | Run 29130 | |
|---|---|---|---|---|---|
| Element | Theoretical | Found | Diff | Found | Diff |
| C | 41.75% | 45.45% | 3.7 | 45.3% | 3.55 |
| H | 2.92% | 2.8% | −0.12 | 2.93% | 0.01 |
| N | 8.11% | 8.51% | 0.4 | 8.47% | 0.36 |

As indicated in Tables 1-2, a representative sample of Formula I comprises 15.73% copper. Given this data, one can calculate the amount of copper in a particular dose of Formula I. For example, a 2.5 mg dose (i.e. one capsule) yields 0.39 mg of copper. Similarly, a 10 mg dose (the preferred dose) yields 1.57 mg of copper. As will be readily apparent to one skilled in the art, however, the actual percentage of copper present in any given sample of Formula I will vary depending on a number of factors including, but not limited to, the purity, consistency and source of the sample, as well as the synthetic methodology employed to obtain the sample.

Figure 1:
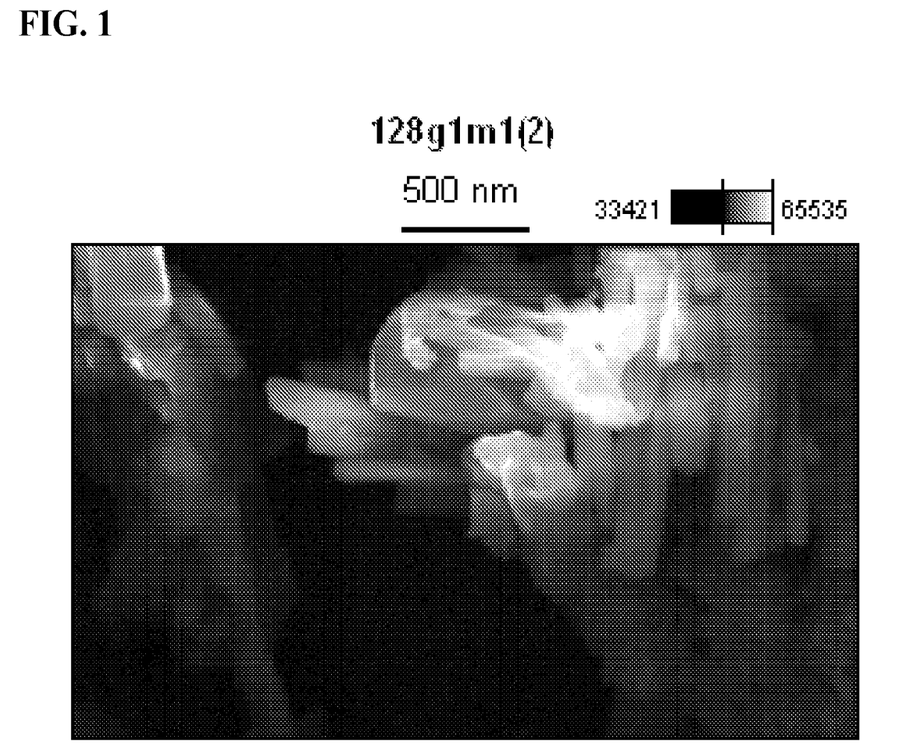
FIG. 1 Depicts imagery obtained from Scanning Electron Microscope (SEM) analysis of a preferred embodiment of the present invention.
Figure 2:
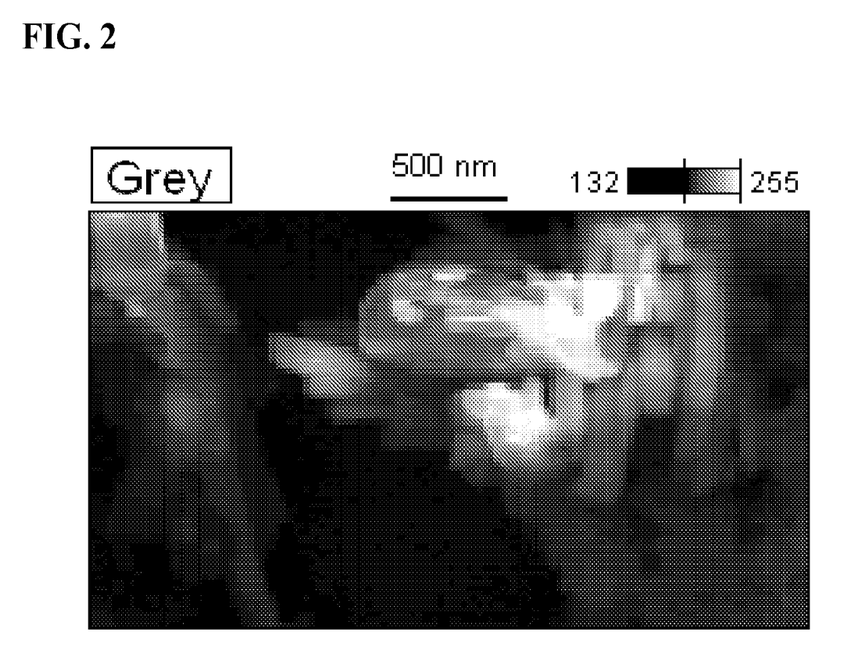
FIG. 2 Depicts imagery obtained from Scanning Electron Microscope (SEM) analysis of a preferred embodiment of the present invention.
Figure 3:
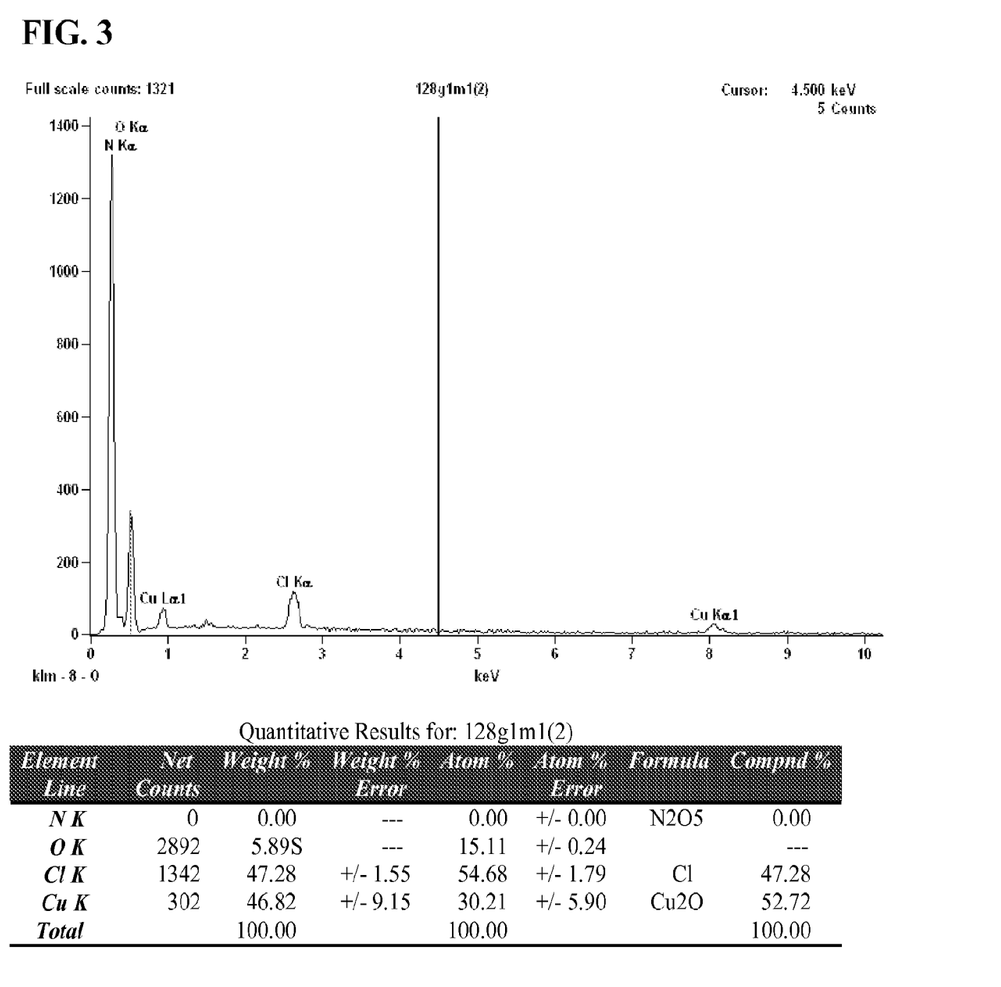
FIG. 3 Shows the quantitative results obtained by mass spectrometry analysis of a preferred embodiment of the composition of the invention.
Figure 4:
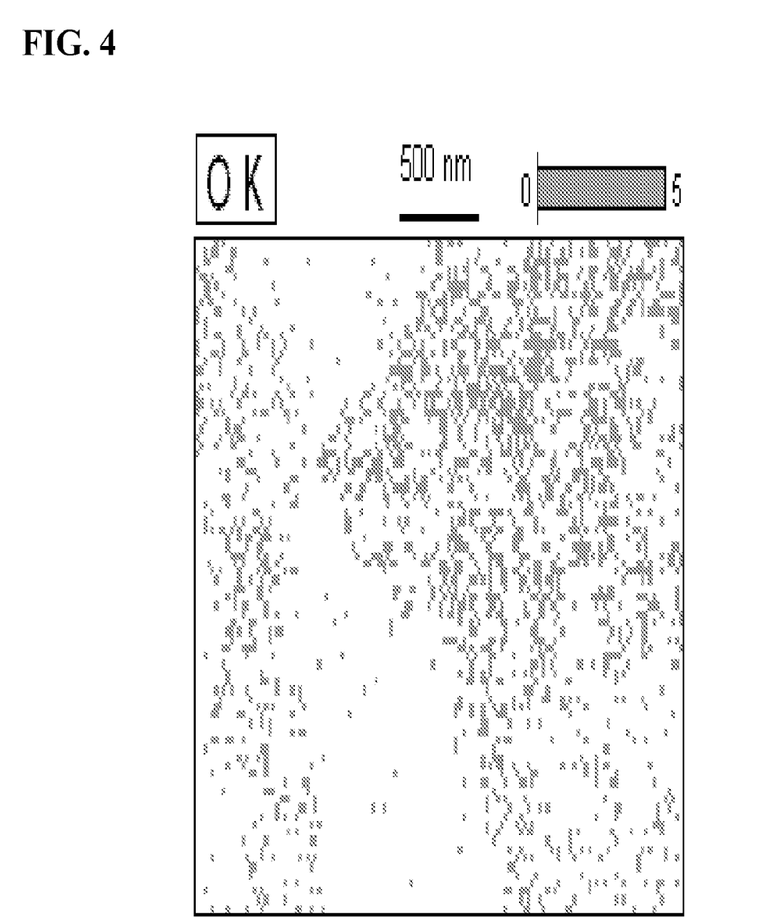
FIG. 4 Shows the O K results obtained by mass spectrometry analysis of a preferred embodiment of the composition of the invention.
Figure 5:
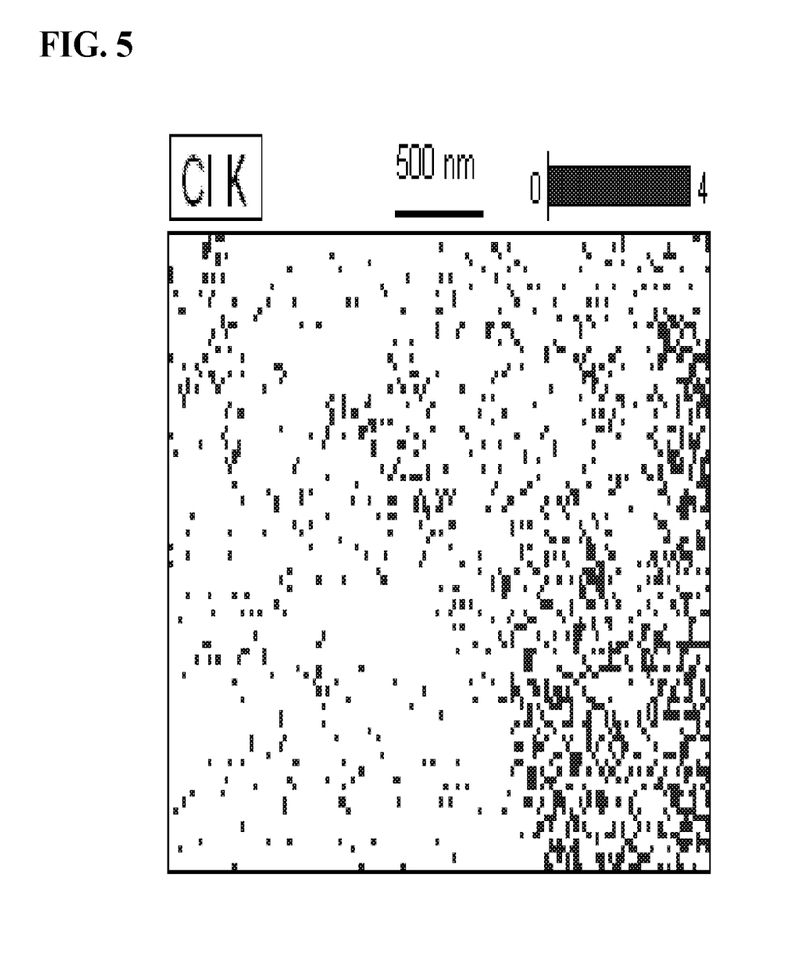
FIG. 5 Shows the Cl K results obtained by mass spectrometry analysis of a preferred embodiment of the composition of the invention.
Figure 6:
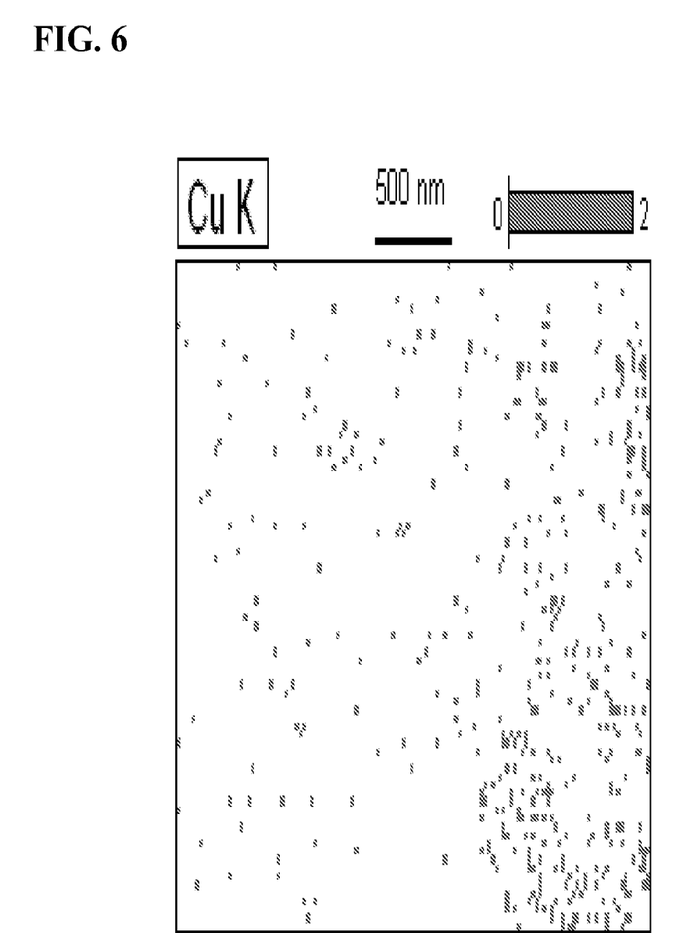
FIG. 6 Shows the Cu K results obtained by mass spectrometry analysis of a preferred embodiment of the composition of the invention.
Figure 7:
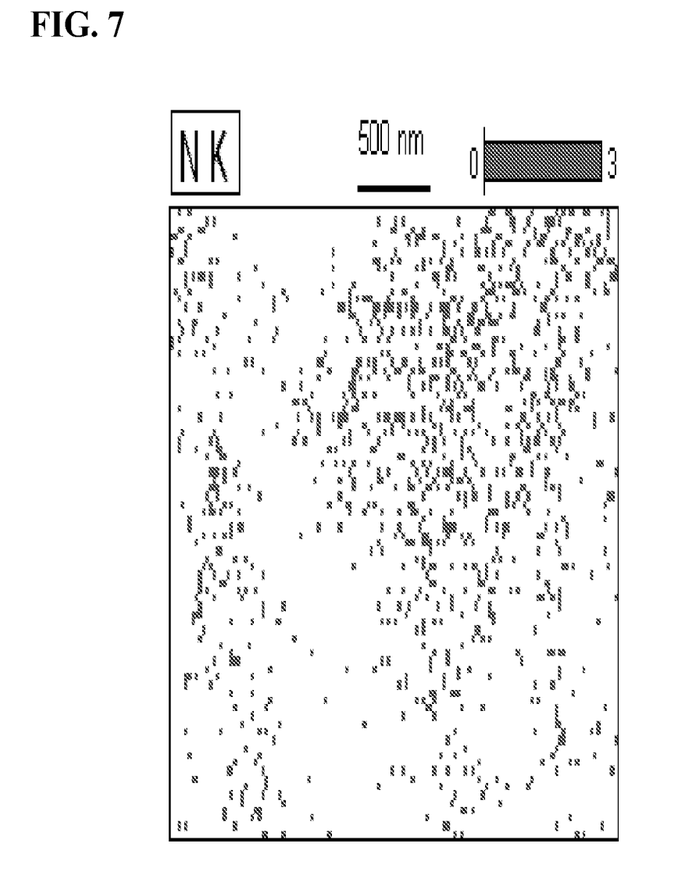
FIG. 7 Shows the N K results obtained by mass spectrometry analysis of a preferred embodiment of the composition of the invention.
Figure 8:
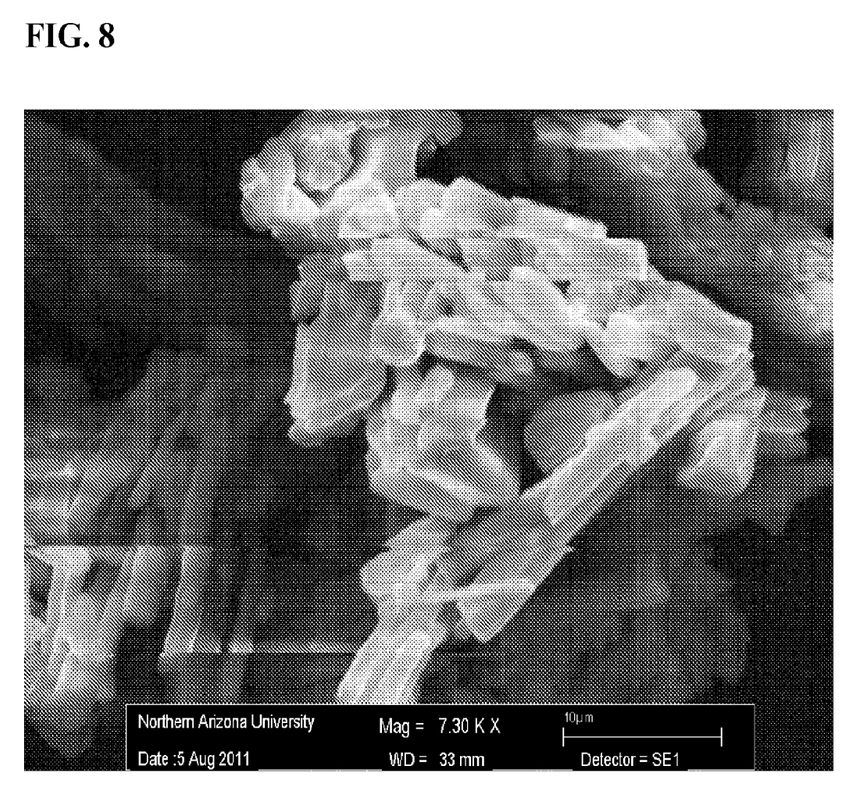
FIG. 8 Depicts imagery obtained from Scanning Electron Microscope (SEM) analysis of a preferred embodiment of the present invention.
Figure 9:
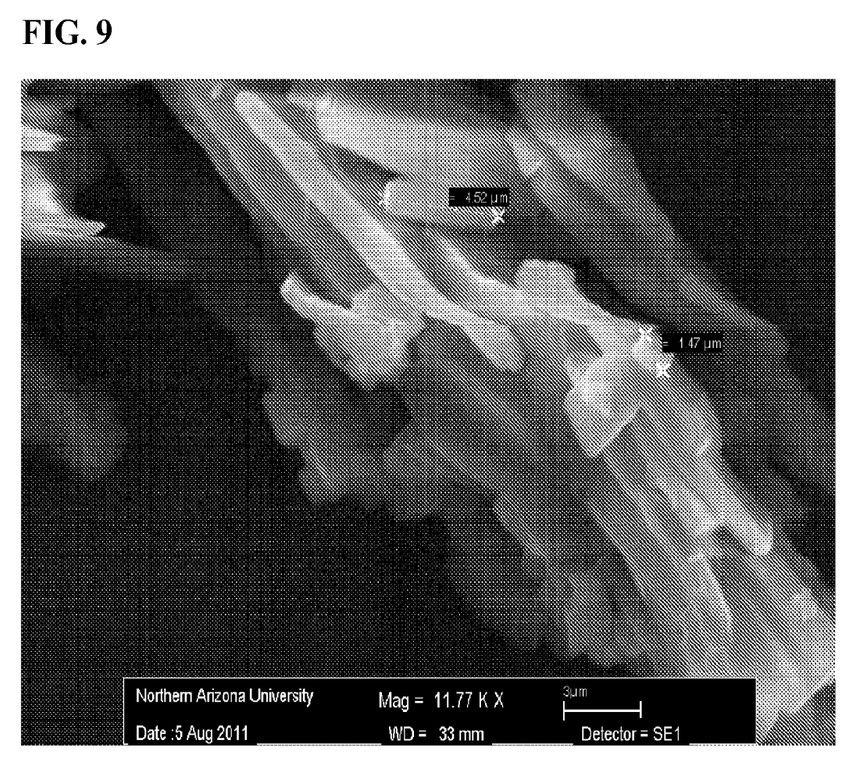
FIG. 9 Depicts imagery obtained from Scanning Electron Microscope (SEM) analysis of a preferred embodiment of the present invention.

FIGS. 1-9 depict data and imagery obtained from Scanning Electron Microscope (SEM) and spectrometer analysis of a preferred embodiment of the present invention. As shown in FIG. 9, the copper particles are approximately 1.4 micrometers (μm) in size.

EXAMPLE

Preparation of Formula I

Those skilled in the art will recognize various synthetic methodologies that may be employed to prepare non-toxic pharmaceutically acceptable compositions of Formula I. One such (representative) example is set forth below:

A 3 L 3-neck round bottomed flask equipped with a mechanical stirrer, reflux condenser and a solid addition funnel was charged with nicotinic acid (131.61 g, 1.07 mol), ascorbic acid (21.4 g, 0.12 mol) and 90% aqueous ethanol (2 L) then placed in an appropriately sized heating mantle. The resultant white suspension was stirred and heated gently to 45° C. and cuprous chloride (35.2 g 0.36 mol) was introduced via the addition funnel over 15 minutes while maintaining an inert atmosphere of Nitrogen throughout the system. During previous experiment attempts, an ethanolic suspension of cuprous chloride was introduced to the reaction mixture as described in Patent Application WO/2010/009739, however, partial oxidation to Copper (II) chloride was observed during addition. To avoid such oxidation, the cuprous chloride was added via the aforementioned 'screw-mechanism' solid addition funnel and no oxidation to Copper (II) chloride was observed. The mixture was then placed under reflux and stirring was continued for a further 4.5 hours. Heating under reflux conditions was maintained for 4.5 hours rather than the recommended 5 minutes to ensure complete complexation. Previous experiment attempts had shown incomplete reaction following just 5 minutes of stirring. Upon cooling to 50° C., the mixture was filtered under suction and the red filter cake was washed with aqueous ascorbic acid 5% w/v solution (400 mL), ethanol 90% (400 mL) and then acetone (100 mL). The red filter cake was then collected and dried en vacuo to afford a red solid (123 g).

It is to be understood that the method set forth hereinabove describes a preferred synthetic methodology and that modifications thereto may be made without departing from the scope or spirit of the invention. Such scope is limited only by the claims below as read in connection with the above specification. May additional synthetic methodologies and additional advantages of applicant's invention will be apparent to those skilled in the art from the above descriptions and the claims below.

We claim:

1. A method of treating lyme disease comprising administering to an animal in need of such treatment a copper complex of formula $C_{12}H_{10}ClCuN_2O_4$, wherein the copper complex is anhydrous and has a chemical structure of Formula (I):

2. The method of claim 1, wherein the animal is a human being and the copper complex is administered sublingually.

3. The method of claim 2, wherein the compound is administered in a dose between 1 mg and 20 mg per day.

4. The method claim 3, wherein the compound is administered in a dose between 5 mg and 10 mg per day.

5. A method of making an anhydrous copper complex having a chemical structure of Formula (I):

comprising the steps of:
   a) adding an effective amount of nicotinic acid, ascorbic acid, and 90% aqueous ethanol to a container;
   b) applying heat to said container;
   c) stirring the contents of the container;
   d) adding cuprous chloride to the container;
   e) refluxing and stirring the contents of the container;
   f) cooling the contents of the container;
   g) filtering out the contents of the container;
   h) washing the filtered contents of the container with aqueous ascorbic acid;
   i) washing the filtered contents with 90% aqueous ethanol;
   j) washing the filtered contents with acetone; and
   k) drying the filtered contents;
wherein the method is performed in an atmosphere consisting of an inert gas.

* * * * *